United States Patent [19]

Vandewalle et al.

[11] 4,341,864
[45] Jul. 27, 1982

[54] PHOTOGRAPHIC ELEMENTS CONTAINING CYAN-FORMING COUPLERS

[75] Inventors: Jan J. Vandewalle; Marcel J. Monbaliu, both of Mortsel; Raphaël K. Van Poucke, Berchem, all of Belgium

[73] Assignee: Agfa-Gevaert, N.V., Mortsel, Belgium

[21] Appl. No.: 243,039

[22] Filed: Mar. 12, 1981

[30] Foreign Application Priority Data

Apr. 9, 1980 [GB] United Kingdom ................ 8011694

[51] Int. Cl.$^3$ ........................ G03C 1/76; G03C 1/40
[52] U.S. Cl. .................................. 430/505; 430/552; 430/553
[58] Field of Search ..................... 430/505, 552, 553

[56] References Cited

U.S. PATENT DOCUMENTS

| | | | |
|---|---|---|---|
| 2,895,826 | 7/1959 | Salminen et al. | 430/552 |
| 3,880,661 | 4/1975 | Lau et al. | 430/552 |
| 4,009,035 | 2/1977 | Kojima et al. | 430/552 |
| 4,012,258 | 3/1977 | Kojima et al. | 430/552 |
| 4,124,396 | 11/1978 | Osborn | 430/553 |
| 4,299,914 | 11/1981 | Fujimatsu et al. | 430/553 |

Primary Examiner—J. Travis Brown
Attorney, Agent, or Firm—A. W. Breiner

[57] ABSTRACT

Cyan-forming color couplers according to the formula:

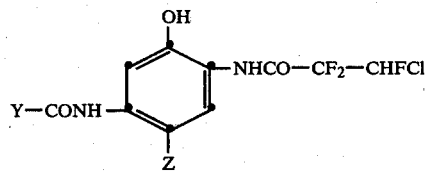

wherein Z is hydrogen in the case of 4-equivalent couplers or a substituent that splits off upon color development, thus conferring a 2-equivalent character to the color coupler, and Y is a ballasting group. These cyan-forming color couplers can be incorporated in (a) red-sensitized silver halide emulsion layer(s) of a photographic multilayer color element or in a non-light-sensitive colloid layer in water-permeable relationship with the red-sensitized emulsion layer(s).

6 Claims, No Drawings

PHOTOGRAPHIC ELEMENTS CONTAINING CYAN-FORMING COUPLERS

The present invention relates to novel cyan-forming colour couplers, to the use thereof in the production of photographic colour images, and to photographic multilayer elements containing such colour couplers.

It is known that for the production of a photographic colour image in a light-sensitive silver halide layer, the exposed silver halide is developed to a silver image by means of an aromatic primary amino compound in the presence of a colour coupler, which reacts with the oxidizied developing substance to form a dyestuff at the areas corresponding to the silver image.

In subtractive three-colour photography use is made of a light-sensitive photographic colour element comprising (a) red-sensitized silver halide emulsion layer(s), (a) green-sensitized silver halide emulsion layer(s), and (a) blue-sensitive silver halide emulsion layer(s), wherein upon colour development, by the use of appropriate colour couplers, cyan, magenta, and yellow dyestuff image are formed respectively.

Fundamental difficulties affecting the subtractive three-colour photographic process are concerned primarily with the stability of the dyes, which make up the coloured photographic images, against light, heat, and humidity. Although colour photography has undergone much improvement since the appearance of the use of coupler compounds for the formation of coloured images, higher dye stability is still wanted.

An important factor in the production of colour images is the cost of the light-sensitive element and consequently of its components and in particular of the colour couplers.

Many attempts have been made to provide new colour couplers having improved characteristics. For instance, the U.S. Pat. No. 2,895,826 discloses a class of colour couplers including cyan-forming couplers, which contain a perfluorobutyramido group and, owing to this group, confer to the dyes formed favourable light absorption characteristics and stability.

A serious drawback of these couplers is that in their preparation, for the introduction of the perfluorbutyramido group, the very expensive perfluorobutyryl chloride has to be used.

DE-OS No. 2,502,820 discloses a class of cyan-forming couplers containing a monohydro-polyfluoroalkyl-carbonamido group according to the formula $-NHCO-CF_2CF_2)_nH$. These couplers are claimed to offer a high solubility and a favourable dispersion stability.

DE-OS No. 2,529,991 teaches the use of cyan-forming couplers containing a $-NHCO-CF_2)_nR$ group, R being hydrogen, alkyl, alkoxy, or aryloxy. These couplers are claimed to be easily and economically accessible as compared with the above-mentioned cyan-forming couplers containing a perfluorobutyramido group.

Yet, both the cyan-forming couplers according to DE-OS No. 2,502,820 and DE-OS No. 2,529,991 are prepared from the relatively expensive starting products of the formula $H(CF_2CF_2)_nCOOH$ and regretfully the two-step synthesis of this class of starting products happens to be rather lengthy and it yields several homologues that need to be separated.

It is an object of the present invention to provide novel cyan-forming colour couplers, which have improved properties and are very interesting from an economical standpoint.

A further object is to provide photographic multilayer colour elements containing said novel cyan-forming colour couplers.

Another object of the invention is to produce a photographic colour image by development of a photographic multilayer colour element containing said novel cyan-forming colour couplers.

Other objects of the invention will become apparent from the disclosure hereinafter.

The above objects are accomplished with the aid of novel fluorine-containing cyan-forming colour couplers, which have been prepared from a comparatively inexpensive starting product, have favourable sensitometric results, and have a high coupling activity, the dyes obtained therewith after coupling being very stable to light, heat, and humidity.

According to the present invention there are provided novel phenol-type colour couplers, capable of forming a cyan indoaniline dye by reaction with an oxidized aromatic primary amino developing agent, said colour couplers comprising a fluorine-containing alkylcarbonamido group, wherein this fluorine-containing alkylcarbonamide group is a 3-chloro-2,2,3-trifluoro-propionamide group in the 2-position of the phenol.

More particularly, in accordance with the present invention there are provided novel cyan-forming colour couplers corresponding to the following general formula:

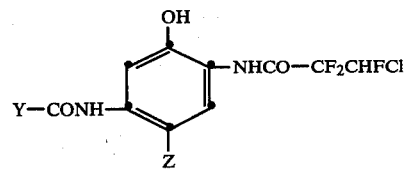

wherein:
Z represents a hydrogen atom in the case of 4-equivalent couplers or a substituent, the so-called coupling off group, that splits off upon colour development, thus conferring to the colour coupler a 2-equivalent character e.g. a halogen atom such as chlorine, an acyloxy group, an alkoxy group, an aryloxy group, an heterocyclocy group, an alkylthio group, an arylthio group e.g. phenylthio and carboxyphenylthio, an alkylsulphonyl group, an arylsulphonyl group, an alkylsulphinyl group, an arylsulphinyl group, an alkyl- or aryl-substituted carbonylmethoxy group, an alkoxy- or aryloxy-substituted carbonylmethoxy group, a heterocyclic thio group such as a tetrazolylthio group, or a phenylazo group,
Y represents a ballasting group, which renders the coupler less liable to diffusion to another colloid layer from a hydrophilic colloid layer, in which it had been incorporated, in particular a group corresponding to the formula:

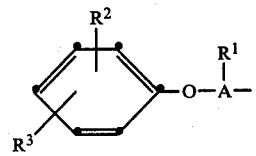

wherein:

A is a $C_1$–$C_5$ alkylene group e.g. methylene or propylene, $R^1$ is hydrogen or a $C_1$–$C_5$ alkyl group e.g. methyl, ethyl, or butyl, $R^2$ is a halogen atom e.g. chlorine, an alkyl group e.g. tert-butyl, tert-pentyl, n-dodecyl, n-tetradecyl, or n-pentadecyl, an alkoxy group e.g. n-dodecyloxy, or a cycloaliphatic group e.g. cyclopentyl, $R^3$ is hydrogen or an alkyl group e.g. tert-butyl, tert-pentyl, or n-tetradecyl, or $R^2$ and $R^3$ together represent the atoms needed to complete a fused on cycloaliphatic ring or a fused on cycloaliphatic ring that is substituted by up to 4 alkyl groups e.g. a tetramethylcyclopentane ring.

The present invention also provides a photographic colour element comprising three silver halide emulsion layers, which are differently optically sensitized and wherein the novel colour coupler(s) are set forth above is (are) present in (a) red-sensitized silver halide emulsion layer(s) or in (a) non-light sensitive colloid layer(s) in water-permeable relationship therewith.

The novel cyan-forming colour couplers containing a 3-chloro-2,2,3-trifluoro-propionamido group are prepared from 3-chloro-2,2,3-trifluoro-propionyl chloride, which is an acid chloride starting product that is far less expensive than the comparable acid chlorides having a perfluoroacyl group.

Representative examples of novel cyan-forming colour couplers, corresponding to the above general formula are given in the following table 1. However, it is to be understood that the invention is not limited to these specifically mentioned colour couplers.

TABLE 1

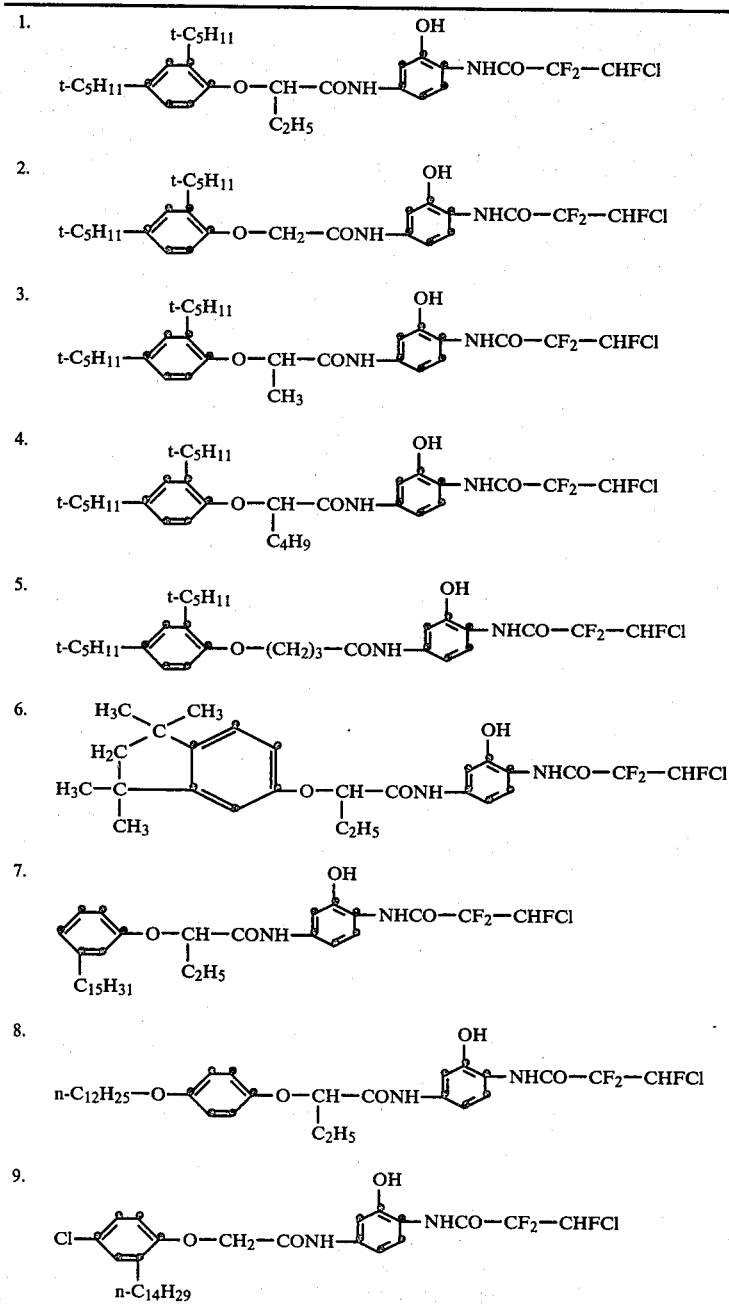

TABLE 1-continued

10. 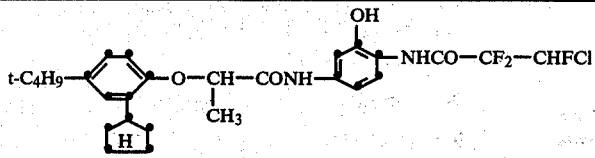

11. 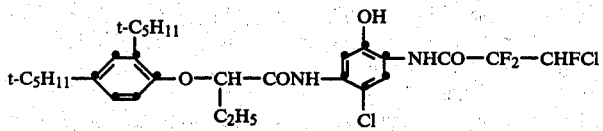

12. 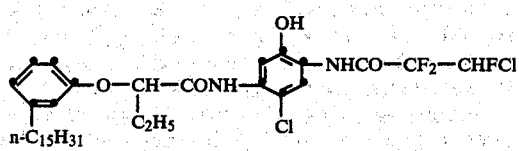

13. 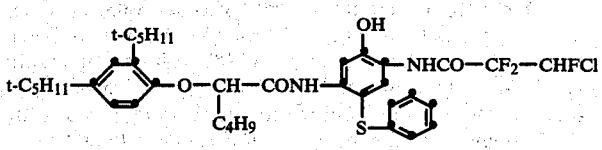

14. 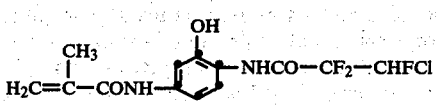

15. 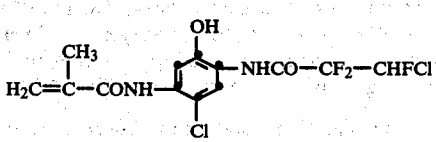

16. 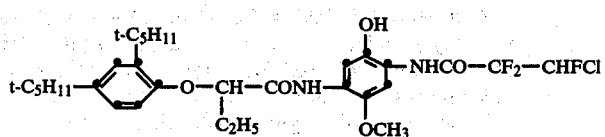

The compounds 1 to 14 can be prepared as described in the preparations hereinafter. The preparation of the other compounds of table 1 as well as of other compounds corresponding to the general formula but not specifically identified herein can be derived from the preparations given hereinafter and will not cause difficulties to those skilled in the art of preparative organic chemistry.

Preparation 1: compound 1

(a) 3-chloro-2,2,3-trifluoro-propionyl chloride

In a three-necked 2 l flask provided with a Vigreux column, a condenser, and a collecting flask were brought 325 g (2 moles) of 3-chloro-2,2,3-trifluoro-propionic acid (Org.Synth.Coll. 5, 239) and 562 g (4 moles) of benzoyl chloride. The mixture was heated so that the acid chloride distilled over slowly. The collected product was refluxed for 20 min to eliminate any residual hydrochloric acid. Finally the product was distilled at normal pressure. Yield: 280 g. Boiling point: 72°–74° C.

(b) 2-(3-chloro-2,2,3-trifluoro-propionamido)-5-nitrophenol 146.8 g (1.1 mole) of anhydrous aluminium chloride were added with stirring to a suspension of 154 g (1 mole) of 2-amino-5-nitrophenol. The brownish black solution was cooled down to 20° C. In 20 min 181 g (1 mole) of 3-chloro-2,2,3-trifluoro-propionyl chloride were added thereto, the temperature being kept at 30° C. by cooling. After 3 hours of stirring at room temperature the solution was poured out in 2 l of icewater and 200 ml of concentrated hydrochloric acid. Stirring was continued for 1 hour. The precipitate was collected and rinsed with water until free from acid.

Yield: 214 g. Melting point: 167° C.

(c) 2-(3-chloro-2,2,3-trifluoropropionamido)-5-aminophenol

In an autoclave 267 g (0.895 mole) of compound (b), 18 ml of Raney-nickel suspension, and 1.3 l of ethanol were placed. The nitro group was reduced with hydrogen at a temperature of 65°–70° C. and an initial pressure of 100–105 bar. After 90 min the required amount of hydrogen had been taken up. The solution was let off and after filtering of the Raney nickel concentrated by evaporation. The dry residue was dissolved in 310 ml of boiling methanol, filtered, and diluted with 360 ml of water.

Yield: 200 g. Melting point: 146° C.

(d) compound 1:
2-(3-chloro-2,2,3-trifluoropropionamido)-5-[2-(2,4-di-tert-pentylphenoxy)-butyramido]-phenol A solution of 33.85 g (0.1 mole) of 2-(2,4-di-tert-pentylphenoxy)butyryl chloride in 80 ml of dioxan was added to a solution of 26.85 g (0.1 mole) of 2-(3-chloro-2,2,3-trifluoropropionamido)-5-aminophenol and 23.7 ml (0.2 mole) of quinoline in 500 ml of dioxan at room temperature. The mixture was stirred for 90 minutes and left standing overnight. Next it was poured out in 2 l of icewater and 100 ml of concentrated hydrochloric acid. The sticky residue was extracted with ether, rinsed with water until free from acid, and dried. The solvent was evaporated and the residue recrystallized from hexane.

Yield: 46 g. Melting point: 160° C.

Preparation 2–10: compounds 2–10

Compounds 2 to 10 were prepared analogously to compound 1 by making 2-(3-chloro-2,2,3-trifluoropropionamido)-5-aminophenol (compund (c) of preparation 1) react with the acid chlorides listed in the following table 2 to introduce the appropriate substituent in the 5-position of the phenol. The melting point of the colour couplers obtained with the acid chlorides given is mentioned as well.

TABLE 2

| Acid chloride | Used to form compound no. | Melting point of resulting colour coupler |
| --- | --- | --- |
| 2-(2,4-di-tert-pentylphenoxy)-acetyl chloride | 2 | 191° C. |
| 2-(2,4-di-tert-pentylphenoxy)-propionyl chloride | 3 | 149–150° C. |
| 2-(2,4-di-tert-pentylphenoxy)-hexanoyl chloride | 4 | 159° C. |
| 4-(2,4-di-tert-pentylphenoxy)-butyryl chloride | 5 | 210° C. |
| 2-(1,1,3,3-tetramethyl-5-indanoxy)-butyryl chloride | 6 | 178° C. |
| 2-(3-n-pentadecylphenoxy)-butyryl chloride | 7 | 103° C. |
| 2-(4-n-dodecyloxy-phenoxy)-butyryl chloride | 8 | 115° C. |
| 2-(4-chloro-2-n-tetradecylphenoxy)-acetyl chloride | 9 | 130° C. |
| 2-(4-tert-butyl-2-cyclopentylphenoxy)-propionyl chloride | 10 | 187–188° C. |

The intermediate product 2-(4-n-dodecyloxy-phenoxy)butyryl chloride can be prepared as described hereinafter from 2-(4-n-dodecyloxy-phenoxy)-butyric acid, which itself can be prepared as follows: 2-(4-n-dodecyloxy-phenoxy)-butyric acid In a three-necked 3 l flask provided with a stirrer, a thermometer, a dropping funnel, and a Dufton column were introduced 278 g (1 mole) of 4-n-dodecyloxy-phenol, 1.4 l of anhydrous toluene, and 185 ml (1 mole) of a 30% solution of sodium methanolate in methanol. Whilst heating all of the methanol was distilled off azeotropically. Next, 208 g (1.15 mole) of α-bromobutyric acid methyl ester were added dropwise. The resulting mixture was refluxed for 90 min with stirring and then allowed to cool down for a short time. 400 ml of isopropanol and 300 ml of 5 N sodium hydroxide were added and the mixture obtained was refluxed for 1 hour with thorough stirring. After neutralization with 350 ml of 5 N hydrochloric acid, the toluene layer was decanted. The residue was rinsed with water until free from acid and dried. The solvent was evaporated.

Yield: 360 g. Melting point: 80°–81° C. (recrystallized from hexane: 82° C.).

2-(4-n-dodecyloxy-phenoxy)-butyryl chloride 216 ml of thionyl chloride were added portion-wise in 30 min to 360 g of 2-(4-n-dodecyloxy-phenoxy)-butyric acid. The mixture was refluxed for 2 hours and the remaining thionyl chloride was evaporated completely. A pink oil remained.

Yield: 371 g.

The intermediate product 2-(1,1,3,3-tetramethyl-5-indanoxy)-butyryl chloride can be prepared as described hereinafter from 2-(1,1,3,3-tetramethyl-5-indanoxy)-butyric acid, which itself can be prepared as follows: 2-(1,1,3,3-tetramethyl-5-indanoxy)-butyric acid In the same way as in the case of 2-(4-n-dodecyloxy-phenoxy)-butyric acid all of the methanol was distilled off from a mixture of 89 g (0.468 mole) of 1,1,3,3-tetramethyl-5-indanol, 750 ml of anhydrous toluene, and 86.7 ml (0.468 mole) of a 30% solution of sodium methanolate in methanol. 93.2 g (0.515 mole) of α-bromobutyric acid methyl ester were added to the suspension of the resulting sodium salt of 1,1,3,3-tetramethyl-5-indanol. The mixture was refluxed for 7 hours. 180 ml of isopropanol and 140 ml of 5 N sodium hydroxide were added to the hot (80° C.) mixture and refluxing was then continued for 1 hour. The mixture was cooled down to room temperature and admixed with 164 ml of 5 N hydrochloric acid. The toluene layer was decanted. The residue was dried and the solvent was evaporated.

Yield: 128 g of white product melting at 97° C.

2-(1,1,3,3-tetramethyl-5-indanoxy)-butyryl chloride

A mixture of 100.5 g (0.364 mole) of 2-(1,1,3,3-tetramethyl-5-indanoxy)-butyric acid and 67 ml of thionyl chloride were refluxed for 2 hours. The excess thionyl chloride was evaporated.

Yield: 106 g of a light brown oil.

Preparation 11: compound 11

At room temperature 2.02 ml (0.025 mole) of sulphuryl chloride were added to a solution of 14.26 g (0.025 mole of compound 1 in 62 ml of anhydrous methylene chloride. The mixture was stirred for 1 hour. Next, the solution was concentrated by evaporation and the residue was recrystallized from 30 ml of acetonitrile. The product was collected and dried.

Yield: 12 g. Melting point: 125° C.

Preparation 12: compound 12

Preparation 11 was repeated with compound 7 instead of compound 1. Melting point of compound 12: 119° C.

Preparation 13: compound 13

29.95 g (0.05 mole) of 2-(3-chloro-2,2,3-trifluoropropionamido)-5-[2-(2,4-di-t-pentylphenoxy)-hexanamido]-phenol and a catalytic amount of iron powder were placed in a reaction flask that was completely shielded from light. The mixture was stirred in 65 ml of acetonitrile. Only part of the compound dissolved. The mixture was cooled with an ice-bath. A solution of 8.67 g (0.06 mole) of benzene sulphenyl chloride in 25 ml of acetonitrile was added dropwise in 20 min. The temperature rose to 16° C. and hydrogen chloride escaped. The solution was stirred for 3 hours and left standing overnight. 50 ml of methanol were added. The mixture was stirred. The precipitate was filtered with suction, washed with acetonitrile, and dried.

Yield: 22 g. Melting point: 198° C.

Preparation 14: compound 14

58 g (0.68 mole) of sodium hydrogen carbonate were added to a solution of 161.1 g (0.6 mole) of 2-(3-chloro-2,2,3-trifluoropropionamido)-5-aminophenol in 600 ml of acetonitrile. 61.1 ml (0.63 mole) of methacrylic acid chloride were added dropwise thereto in 30 min at room temperature. The temperature of the resulting suspension was maintained at 40° C. for 1 hour. Next, the suspension was poured out in 2 l of water and 50 ml of concentrated hydrochloric acid. The precipitate was filtered with suction, rinsed with water until free from acid, dried, and stirred in 200 ml of isopropylether.

Yield: 144 g of 2-(3-chloro-2,2,3-trifluoropropionamido)-5-methacryloylamidophenol.

Compound 14 and compound 15, which only differs from compound 14 in that it contains a chlorine coupling-off group, are suited for use as polymeric coupler in the form of a latex obtained by emulsion polymerization techniques with the aid of the usual addition polymerization initiators. Interesting polymerization techniques have been described e.g. in the Belgian Patent Specification No. 669,971, according to which latices are formed of polymeric colour couplers by emulsion polymerization in aqueous gelatin, and in the United Kingdom Patent Specification No. 1,130,581 according to which latices are formed of polymeric couplers by emulsion polymerization in water, as well as in the United Kingdom Patent Specification No. 1,453,057, according to which latices are made of polymeric colour couplers and competing couplers wherein the polymer particles are internally stabilized in the aqueous colloidal dispersion by a polymerically combined emulsifier.

Examples of polymerization initiators and suitable solvents as well as information relating to the formation of the initial emulsions and/or suspensions have been set forth in the above-mentioned patents.

The preparation of a latex polymer from compound 14 of table I can be carried out as follows: 12.5 ml of a 1% by weight solution of the sodium salt of 4,4'-azobis(4-cyanovaleric acid) as an initiator were added to 200 ml of demineralized water at 90° C. The solution was heated to 95° C. Next, 1/6th of a suspension of 40 g of 2-(3-chloro-2,2,3-trifluoropropionamido)-5-methacryloylamido-phenol, 50 ml of 10% N-oleyl-N-methyltauride sodium salt, and 100 ml of water were added at once. In 15 min 1/6th of a mixture of 45 g of ethyl acrylate and 15 g of methacrylic acid were added on the one side and 6.25 ml of the above-mentioned initiator solution were added dropwise on the other side. The temperature was kept at 94°–96° C.

The addition of 1/6th of the above suspension and of the mixture of ethyl acrylate and methacrylic acid as well as 6.25 ml of initiator solution was repeated five times. The mixture was then heated for 30 min at reflux temperature and the latex was concentrated by evaporation for 10%.

Yield: 452 g of latex polymer of 2-(3-chloro-2,2,3-trifluoropropionamido)-5-methacryloylamidophenol, ethyl acrylate, and methacrylic acid.

Concentration of solids per 100 g of latex: 21.4 g.
Concentration of polymer per 100 g of latex: 20.1 g.

The cyan-forming colour couplers according to the present invention are of the non-diffusing type and therefore comprise in their molecule an organic group sufficiently large to prevent the colour coupler from wandering from the colloid layer, in which the colour coupler has been incorporated, to another colloid layer.

For the preparation of a photographic multiplayer colour element the non-diffusing colour couplers for each of the colour separation images are usually incorporated into the coating compositions of the differently sensitized silver halide emulsion layers. Yet, the non-diffusing colour couplers can also be added to the coating compositions of non-light-sensitive colloid layers that are in water-permeable relationship with the light-sensitive silver halide emulsion layers.

During the preparation of the light-sensitive colour element the non-diffusing cyan-forming colour couplers according to the above general formula can be incorporated into the coating composition of the silver halide emulsion layers or other colloid layers in water-permeable relationship therewith according to any technique known by those skilled in the art for incorporating photographic ingredients, more particularly colour couplers, into colloid compositions.

The cyan-forming colour couplers according to the invention can be dispersed, occasionally in the presence of a wetting or dispersing agent, in a hydrophilic composition constituting or forming part of the binding agent of the colloid layer. Very suitable wetting agents that can be used to disperse the cyan-forming colour couplers of the invention are the fluorine-containing surface active agents of U.K. Patent Application No. 79/07040 filed on Feb. 28, 1979. For more details about particularly suitable techniques that can be employed for incorporating the colour couplers of the invention into a hydrophilic colloid layer of a photographic element there can be referred to U.K. Patent Specification Nos. 791,219—1,098,594—1,099,414—1,099,415—1,099,416—1,099,417—1,199,570—1,218,190—1,297,947, to the U.S. Pat. Nos. 2,269,158—2,284,887—2,304,939—2,304,940—2,322,027, to the French Patent Specification No. 1,555,663, and Belgian Patent Specification No. 722,026.

Another technique for incorporating colour couplers is via polymeric latices as described in the published German Patent Applications DE-OS Nos. 2,541,230 and 2,541,274 and as referred to hereinbefore.

The cyan-forming colour couplers according to the invention can be used in conjunction with various kinds of photographic emulsions. Various silver salts can be used as the light sensitive salt. For instance silver bromide, silver iodide, silver chloride or mixed silver halides such as silver chlorobromide, silver bromoiodide, and silver chlorobromoiodide can be employed. The couplers can be used in emulsions of the mixed packet type as described in the U.S. Pat. No. 2,698,794 or emulsions of the mixed grain type as described in the U.S. Pat. No. 2,592,243. The colour couplers can be used with emulsions wherein the latent images are formed predominantly at the surface of the silver halide crystal or with emulsions wherein latent images are formed predominantly inside the silver halide crystal.

The hydrophilic colloid used as the vehicle for the silver halide can be e.g. gelatin, colloidal albumin, zein, casein, a cellulose derivative, a synthetic hydrophilic colloid such as polyvinyl alcohol or poly-N-vinyl pyrrolidone. If desired, compatible mixtures of two or more of these colloids can be employed for dispersing the silver halide.

The light-sensitive silver halide emulsions used in the preparation of a photographic material according to the present invention can be sensitized chemically as well as optically. They can be sensitized chemically by carrying out the ripening in the presence of small amounts of sulphur-containing compounds such as allyl thiocyanate, allyl thiourea, or sodium thiosulphate. The emulsions can also be sensitized by means of reducing agents e.g. tin compounds as described in the French Patent Specification No. 1,146,955 and in Belgian Patent Specification No. 568,687, imino-aminomethane sulphinic acid compounds as described in U.K. Patent Specification No. 789,823 and small amounts of noble metal compounds such as gold, platinum, palladium, iridium, ruthenium, and rhodium compounds. They can be sensitized optically by means of cyanine and merocyanine dyes.

The said emulsions can also comprise compounds that sensitize the emulsions by development acceleration e.g. compounds of the polyoxyalkylene type such as alkylene oxide condensation products as described i.a. in U.S. Pat. Nos. 2,531,832—2,533,990, in U.K. Patent Specification Nos. 920,637—940,051—945,340—991,608 and 1,091,705 and onium derivatives of amino-N-oxides as described in U.K. Patent Specification No. 1,121,696.

Further, the emulsions may comprise stabilizers e.g. heterocyclic nitrogen-containing thioxo compounds such as benzothiazoline-2-thione and 1-phenyl-2-tetrazoline-5-thione and compounds of the hydroxytriazolopyrimidine type. They can also be stabilized with mercury compounds such as the mercury compounds described in Belgian Patent Specification Nos. 524,121—677,337, and in the U.K. Patent Specification No. 1,173,609.

The light-sensitive emulsions containing the colour couplers of the invention may also comprise any other kind of ingredient such as those described for such emulsions in Research Disclosure no. 17 643 of December 1978, in particular development-inhibitor-releasing compounds and competing couplers. Such compounds and couplers can be incorporated in layers in water-permeable relationship with the emulsion layers containing the couplers of the present invention.

The non-diffusing cyan-forming colour couplers of the present invention are usually incorporated into a red-sensitized silver halide emulsion for forming one of the differently sensitized silver halide emulsion layers of a photographic multilayer colour element. Such photographic multilayer colour element usually comprises a support, (a) red-sensitized silver halide emulsion layer(s) with cyan-forming colour coupler, (a) green-sensitized silver halide emulsion layer(s) with (a) magenta-forming colour coupler, and (a) blue-sensitive silver halide emulsion layer(s) with yellow-forming colour coupler.

The emulsions can be coated on a wide variety of photographic emulsion supports. Typical supports include cellulose ester film, polyvinylacetal film, polystyrene film, polyethylene terephthalate film and related films or resinous materials, as well as paper and glass.

For the production of photographic colour images according to the present invention an exposed silver halide emulsion layer is developed with an aromatic primary amino developing substance in the presence of a colour coupler according to the present invention. All colour developing agents capable of forming azomethine dyes can be utilized as developers. Suitable developing agents are aromatic compounds in particular p-phenylene diamines, e.g. N,N-diethyl-p-phenylene diamine, N,N-dialkyl-N'-sulphomethyl-p-phenylene diamines and N,N-dialkyl-N'-carboxymethyl-p-phenylene diamines.

In photographic colour systems, according to which image dyes are formed by reaction of an image pattern of an oxidized p-phenylene diamine colour developing agent with a dye-forming coupler e.g. one of the cyan-forming couplers according to the present invention, the developed metallic silver and residual silver salts are removed as a rule. This can be realized by separate bleaching and fixing steps, though processing is simplified by the use of a bath often called blix bath or bleach fix bath which bleaches and fixes in one single processing operation.

A bleach fix bath contains known fixing agents for silver halide e.g. alkali metal thiosulphates or ammonium thiosulphate, and an oxidizing agent e.g. a complex salt of an alkali metal and trivalent iron with an organic acid e.g. the tetra-sodium salt of ethylene diamine tetra-acetic acid (EDTA). It is known to improve the effectiveness of a bleach fix bath by addition thereto of a polyethylene oxide acid (or a derivative thereof, or of a polyalkylene oxide in which some of the oxygen atoms have been replaced by sulphur atoms, e.g. the polyalkylene oxide derivatives described in the U.K. Patent Specification No. 933,008.

Other interesting blix activators or bleach activators that can be used in bleach fix baths or bleach baths containing EDTA-complex salts are oxathioethers corresponding to the following general formula:

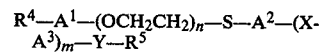

wherein:
R$^4$ represents hydrogen, a C$_1$–C$_4$ alkyl group e.g. methyl, a C$_1$–C$_4$ alkyl group substituted by one or more hydroxy groups, or the group R$^5$—Y—(A$^3$—X)$_m$—A$^2$—S—,
A$^1$, A$^2$, and A$^3$ (same or different) each represent a C$_1$–C$_5$ alkylene group, e.g. ethylene, with the proviso that A$^1$ is a chemical monovalent bond when R$^4$ is hydrogen, a C$_1$–C$_4$ alkyl group, or a substituted C$_1$–C$_4$ alkyl group,
X represents —OCO—, —SO$_2$—, —CONH—, or the group Y,
Y represents a ligand or complexing function of the type of —S— and —N(Q)—, Q being hydrogen or alkyl,
R$^5$ represents a C$_1$–C$_4$ alkyl group e.g. methyl or a C$_1$–C$_4$ alkyl group substituted by one or more hydroxy groups e.g. hydroxyethyl or dihydroxypropyl, or when Y is —N(Q)—, R$^5$ may represent together with Q the atoms necessary to complete a nitrogen-containing saturated ring e.g. a morpholino ring or a piperidino ring,
n is a positive whole number of at least 2, and
m is 0 or 1.

Preferred representatives of blix or bleach activators corresponding to the above general formula, which can be used in silver-salt-sensitized colour photographic systems in accordance with the invention, are the compounds listed in the following table.

TABLE 3

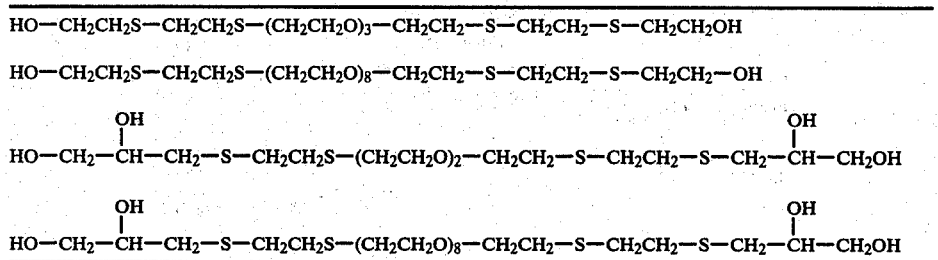

These compounds can be prepared e.g. by conversion of a mono- or bis-toluene sulphonic acid ester of a polyethylene glycol having the desired molecular weight with a mercaptoalkanol into the corresponding oxathia-alkane-diol. The terminal hydroxy group(s) of the alkane-diol can be converted with thionyl chloride into chloro groups. The dichloro compound can then be made to react with appropriate mercapto-alkanols to form compounds of the type listed in Table 3.

The following examples illustrate the present invention.

EXAMPLE 1

114.6 g of a red-sensitized silver bromoiodide emulsion (2.3 mole % of iodide) comprising per kg an amount of 73.4 g of gelatin and an amount of silver halide equivalent to 47 g of silver nitrate were diluted with 127 g of a 7.5% by volume solution of gelatin in 100 ml of distilled water.

A dispersion of cyan-forming colour coupler was made by dissolving 0.006 mole of the colour coupler as specified in the table hereinafter in 16 ml of ethyl acetate and 2 g of dibutylphthalate, dispersing the resulting solution in 100 ml of a 5% by volume aqueous solution of gelatin containing 0.4 g of the sodium salt of dodecyl-benzene sulphonic acid by means of an ultrasonic power generator, and eliminating the ethyl acetate by evaporation under reduced pressure.

The resulting dispersion was added to the red-sensitized silver halide emulsion.

After neutralization of the emulsion and addition thereto of the usual additives such as stabilizing agents e.g. 5-methyl-7-hydroxy-s-triazolo[1,5-a]pyrimidine, wetting agents, and hardening agents the necessary amount of distilled water to obtain 575 g of emulsion was added.

The emulsion was coated on a film support in a ratio of 150 g per sq.m. The emulsion layer was dried and covered with a gelatin antistress layer. The dried emulsion material was cut and the resulting strips were exposed in a Herrnfeld sensitometer for 1/20th second through a continuous wedge with a constant of 0.30. The exposed strips were colour-developed, bleached, fixed, and washed in the conventional way using three different types of developers viz.

the first developer containing as developing agent 2-amino-5-diethylamino-toluene hydrochloride (CD-2); development time: 10 min; temperature of development: 24° C., the second containing as developing agent 4-amino-N-ethyl-N-($\beta$-methanesulphonamidoethyl)-m-toluidine sesquisulphate monohydrate (CD-3); development time: 15 min; temperature of development: 21° C., and the third containing as developing agent 4-amino-3-methyl-N-ethyl-N-($\beta$-hydroxyethyl) aniline sulphate (CD-4); development time: 10 min; temperature of development: 25° C.

In table 4 hereinafter the values of speed, gradation and maximum density obtained after processing with the above-mentioned 3 developers of the strips of red-sensitized emulsion containing the cyan-forming couplers are given.

TABLE 4

| cyan-forming coupler in red-sensitized emulsion | sensitometric results | | | | | | | | |
|---|---|---|---|---|---|---|---|---|---|
| | CD-2 | | | CD-3 | | | CD-4 | | |
| | speed | gradation | $D_{max}$ | speed | gradation | $D_{max}$ | speed | gradation | $D_{max}$ |
| comparison coupler A* | 100 | 1.6 | 3.3 | 100 | 1.8 | 2.9 | 100 | 1.7 | 2.6 |
| coupler 7 | 316 | 2.6 | 3.6 | 251 | 3.5 | 3.7 | 79 | 2.6 | 3.6 |
| coupler 8 | 79 | 2.4 | 3.6 | 100 | 2.5 | 3.6 | 100 | 2.1 | 3.2 |
| coupler 4 | 316 | 1.9 | 3.6 | 100 | 2.6 | 3.5 | 100 | 1.8 | 2.9 |

*comparison coupler A = 5-[α-(2,4-di-tert-pentylphenoxy)hexanamido]-2-heptafluorobutyramidophenol, which is a coupler according to the U.S. Pat. Specification 2,895,826.

The speed was measured at 0.2 above fog. The values given for the speed are relative values, a value of 100 being given to the emulsion containing the comparison coupler A.

It appears from the results in table 4 that in general the speed, gradation, and maximum density of the materials containing the coupler compounds according to the invention are at least as good as those of the materials containing the comparison coupler A. The couplers of the invention, however, are prepared from far less expensive starting materials.

EXAMPLE 2

Example 1 was repeated with the difference that the latex of coupler 14 prepared as described hereinbefore was used as colour coupler in an amount corresponding to 0.006 mole of monomeric coupler 14.

Processing occurred by means of the CD-3 developer as described in example 1.

The results of speed, gradation and maximum density are listed in table 5.

TABLE 5

| cyan-forming coupler in red-sensitized emulsion | sensitometric results | | |
| --- | --- | --- | --- |
| | CD-3 | | |
| | speed | gradation | $D_{max}$ |
| comparison coupler A* | 100 | 1.8 | 2.9 |
| latex of coupler 14 | 79 | 2.3 | 3.7 |

*comparison coupler A: see example 1

We claim:

1. Photographic element comprising (a) light-sensitive silver halide emulsion layer(s) and at least one phenol-type colour coupler capable of forming a cyan indoaniline dye by reaction with an oxidized aromatic primary amino developing agent and comprising a fluorine-containing alkylcarbonamido group, wherein said fluorine-containing alkylcarbonamido group is a 3-chloro-2,2,3-trifluoro-propionamido group in the 2-position of the phenol.

2. Photographic element according to claim 1, wherein said colour coupler corresponds to the following general formula:

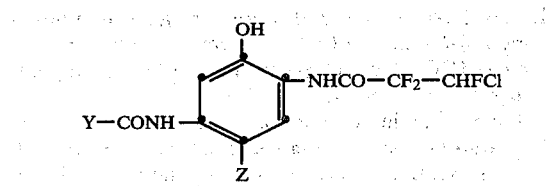

wherein:

Z represents hydrogen or a coupling off group, and
Y represents a ballasting group, which renders the coupler less liable to diffusion to another colloid layer from a hydrophilic colloid layer, in which it had been incorporated.

3. Photographic element according to claim 2, wherein Z is selected from the group consisting of a halogen atom, an acyloxy group, an alkoxy group, an aryloxy group, an heterocycloxy group, an alkylthio group, an arylthio group, an alkylsulphonyl group, an arylsulphonyl group, an alkylsulphinyl group, an arylsulphinyl group, an alkyl- or aryl-substituted carbonylmethoxy group, an alkoxy- or aryloxy-substituted carbonylmethoxy group, a heterocyclic thio group, and a phenylazo group.

4. Photographic element according to claim 2, wherein Y represents a ballasting group corresponding to the general formula:

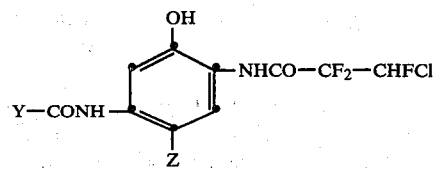

wherein:

Z represents hydrogen or a coupling off group, and
Y represents a ballasting group, which renders the coupler less liable to diffusion to another colloid layer from a hydrophilic colloid layer, in which it had been incorporated.

5. Photographic multilayer colour element comprising in one of the light-sensitive silver halide emulsion layers or in a non-light-sensitive water-permeable colloid layer in water-permeable relationship with the light-sensitive silver halide emulsion layer at least one phenol-type colour coupler capable of forming a cyan indoaniline dye by reaction with an oxidized aromatic primary amino developing agent and comprising a fluorine-containing alkylcarbonamido group, wherein said fluorine-containing alkylcarbonamido group is a 3-chloro-2,2,3-trifluoro-propionamido group in the 2-position of the phenol.

6. Photographic multilayer colour element comprising at least three silver halide emulsion layers, which are differently optically sensitized, a red-sensitized silver halide emulsion layer thereof or a non-light-sensitive colloid layer in water-permeable relationship therewith incorporating at least one phenol-type colour coupler capable of forming a cyan indoaniline dye by reaction with an oxidized aromatic primary amino developing agent and comprising a fluorine-containing alkylcarbonamido group, wherein said fluorine-containing alkylcarbonamido group is a 3-chloro-2,2,3-trifluoropropionamido group in the 2-position of the phenol.

* * * * *